United States Patent [19]
ElSohly et al.

[11] Patent Number: 5,252,490
[45] Date of Patent: Oct. 12, 1993

[54] METHOD OF IDENTIFYING COUNTRY OF ORIGIN OF CANNABIS

[75] Inventors: Mahmoud A. ElSohly, Oxford, Miss.; Rudolf M. Brenneisen, Berne, Switzerland

[73] Assignee: University of Mississippi, University, Miss.

[21] Appl. No.: 429,767

[22] Filed: Oct. 31, 1989

[51] Int. Cl.$^5$ ............................................. G01N 33/00
[52] U.S. Cl. ..................... 436/93; 436/161; 436/901
[58] Field of Search ................... 436/93, 901, 815, 161

[56] References Cited

PUBLICATIONS

Hanus, "Marihuana Cannabis-Sativa L. by Thin Layer Chromatography)", ACTA Univ Palacki Olomuc Fac Med 116(0), 1987 (abstract only) pp. 15–24.

Brenneisen et al, "Chromatographic and Spectroscopic Profiles of Cannabis of Different Orgins", J. Forensic Sci 33(6), 1988 1385–1404 (Abstract Only).

Baker, "Variations in the THC Content in Illicity Imported Cannabis Products", Bull Narc. 1980, 32(4) pp. 47–54 (Abstract Only).

Maundin, "The Farensic Significance of the Age and Origin of Cannabis", Med. Sci. Law. (England), 1976, 1612 (78–90) (Abstract Only).

Turner et al., "Constituents of *Cannabis sativa* L. II: Absence of Cannabidiol in an African Variant" J. of Pharmaceutical Science vol. 2 No. 2 (Feb. 2, 1973) pp. 251–255.

Holley et al., "Cannabidiol and Cannabichromene in Samples of Known Geographical Origin" J. of Pharmaceutical Science vol. 64, No. 5 (May 1975) pp. 892–895.

Turner et al. "Constituents of *Cannabis sativa* L. VI: Propyl Homologs in Samples of Known Geographical Origin" J. Pharm. Science vol. 62, No. 10 (Oct. 1973) pp. 17-39–17-41.

*Primary Examiner*—Lyle A. Alexander
*Attorney, Agent, or Firm*—William D. Stokes

[57] ABSTRACT

The method of identification of the country of origin of CANNABIS (Marijuana). The method comprises gas chromatographic/mass spectrometric analysis of extracts of multiple samples of marijuana plant material from a country or geographical location, preparing a location profile from the chemical profiles made from analysis of the multiple samples from a specific country or location. The analyzed profile of a sample of unknown origin is compared with the location profiles of the various countries growing marijuana.

10 Claims, No Drawings

ID OF CANNABIS

BRIEF DESCRIPTION OF THE INVENTION

The present invention is directed to a method useful in the identification of the country of origin of CANNABIS (Marijuana), particularly in the determination of the country of origin of marijuana confiscated by seizure of marijuana illegally smuggled into the country. The method involves development of a location profile of samples of marijuana grown in various countries of the world from chemical profiles of such samples.

BACKGROUND OF THE INVENTION

Herbal Cannabis (Cannabis, marijuana), Cannabis resin (hashish), and extracts of Cannabis resin (hashish oil) are still the most abused illicit drugs of the world. It is estimated that over 8,000 tons of Cannabis are being consumed in the United States each year. The majority of this material is smuggled into the country from major Cannabis-producing countries such as Colombia, Mexico, Jamaica, and Thailand. More recently an increase of the domestic production has been observed.

In an effort to combat drug abuse, the current U.S. Administration policy has been multifaceted. One of the major efforts to reduce availability of the drug is through enforcement and interdiction. To have a successful interdiction program, it is important to know where the illicit drug is coming from so that resources can be allocated where most needed to stop shipments. There are reasons to believe that Cannabis from one country is being shipped to the United States through intermediate countries, for example, Colombian or Thai Cannabis through Mexico to the United States. Consequently, a seizure of Cannabis at the Mexican border does not necessarily mean that it originated in Mexico. A procedure to determine the country of origin of a Cannabis sample is thus of great importance in law enforcement and forensic science applications.

Attempts have been made in the past to classify Cannabis based on its country of origin with little success. Turner, C.E.; and Hadley, K.W.; Constituents of *Cannabis sativa L.*, II: Absence of cannabidiol in an African variant, *J. Pharm. Sci.*, 62:251–255, 1973; Turner, C.E.; Hadley, K.W.; and Fetterman, P.S.; Constituents of *Cannabis sativa L.*, VI: Propyl homologs in samples of known geographical origin, *J. Pharm. Sci.*, 62:1739–1741, 1973; and Holley, J.H.; Hadley, K.W.; and Turner., C.E.; Constituents of *Cannabis sativa L.*, XI: Cannabidiol and cannabichromene in samples of known geographical origin, *J. Pharm. Sci.*, 64:892–894, 1975.

Stromberg, L.; Minor components of *Cannabis* resin, III: Comparative gas chromatographic analysis of hashish, *J. Chromatog.*, 68:253–258, 1972; and de Zeeuw, R.A.; Wijsbeek, J.: and Malingre, T.M.; Interference of alkanes in the gas chromatographic analysis of *Cannabis* products, *J. Pharm. Pharmcol.*, 25:21–26, 1973.

None of the methods suggested to date have provided a method for determining geographical origin of marijuana.

This invention deals with the development of a procedure which allows for the distinction of marijuana samples from different countries on the basis of their chemical profiles.

DESCRIPTION OF THE INVENTION

This invention in its preferred embodiment provides a method for chemical analysis of marijuana samples which identifies specific components to be used for classification of the samples according to their country of origin.

The method comprises analyzing multiple samples of marijuana plant material from a country or geographical location by gas chromatographic/mass spectrometric analysis of an extract of the plant material. A chemical profile of each sample is established. A location profile is then prepared from the mean of the profiles of the analysis of the multiple samples from a specific country or geographical location within a country. The mean profile data will allow comparison of the location profiles with the profile of a sample of unknown origin. The data, in the preferred embodiment, is incorporated into a computer program which allows the direct comparison of the location profiles with the chemical profile of a sample of unknown origin. This comparison would lead to a weighted ranking of the fit of the unknown sample profile among the stored location profiles and therefore a decision can be made in reference to the country of origin of the sample under investigation.

The country of origin of a sample of illegal marijuana may be determined by chromatographic/mass spectrometric analysis of the extract of the plant material of unknown origin in the presence of an internal standard and calculation of the relative intensity of each peak in the sample's chromatogram relative to that of the internal standard. The data from this analysis make up the chemical profile for the sample of unknown origin, referred to as the "sample profile" which is then compared with the location profiles for various countries of origin.

In the procedure described in this patent, the samples are to be extracted with an organic solvent. In the preferred embodiment, the solvent used is a mixture of methanol and chloroform in the ratio of 9:1 and the extraction time is 15 minutes under sonication. However, other solvents could be used such as pure chloroform or methanol, and the time could be extended to one hour with or without heat to affect exhaustive extraction.

In the preferred embodiment, the plant extracts are subjected to GC/MS analysis in the underivatized forms. However, derivatization of the extracts prior to analysis could be made. Such derivatives include, but are not limited to, the trimethylsilyl derivatives and the acetate derivatives.

In the preferred embodiment, the internal standard used is phenanthrene as 0.2 mg/ml in the extraction solvent. However, other internal standards such as 4-androstene-3,7-dione or any appropriate hydrocarbon could be used over a wide concentration range.

Furthermore, in the preferred embodiment the analysis of the extracts is carried out using gas chromatography/mass spectrometry. However, other gas chromatographic detection methods could be used such as flame ionization detector. The chromatographic column used in the preferred embodiment is a 30 M ×0.25 mm internal diameter DB-1 column (cross linked and bonded 100% dimethyl-polysiloxane phase). However, other chromatographic colums could be used such as DB-5 (cross linked and bonded, 5% phenyl, 95% dimethyl polysiloxane phase) or equivalent of either column. It is imperative, however, that the same columns and conditions used to generate the location profile be used to generate the profile for the sample under investigation.

EXAMPLE I

Chemical Profile of Cannabis samples from Colombia

Several samples of marijuana obtained from Colombia (at least 25 samples) are used for the generation of chemical profiles of Colombia Cannabis. Each sample was extracted and analyzed as follows:

One hundred (100) mg of each dried and powdered sample were extracted with 1 mL of methanol-chloroform (9:1) containing 0.2 mg/ml phenanthrene as internal standard by sonication for 15 minutes. For gas chromatographic/mass spectrometric analysis (GC/MS), 100 ul of the extract was diluted with 900 uL of methanol and aliquots of 1 uL were injected. The GC/MS conditions were as follows: A Varian 3300 gas chromatograph (Varian Instruments, Palo Alto, CA) fitted with a Durabond fused silica capillary column (30 M$\times$0.25 mm I.D.) coated with DB-1 (J & W Scientific, Inc., Rancho Cordova, CA) at a film of 0.25 um was used and operated in the splitless mode (split vent activation time of 30 seconds). The GC column was connected to the mass spectrometer (a Finnigan Ion Trap Detector (ITD) System, Finnigan MAT, San Jose, CA) through an open split interface or by direct interface. The ITD system was operated with Software Version 3.0. The temperature of the transfer line and the ITD manifold was set at 250° C. and 220° C. respectively.

The scan range was from m/z 55 to 450, and the scan rate was set at 1 scan/second. The GC oven temperature was programmed from 70° to 250° C. at rate of 5° C./minute. The injection temperature was maintained at 250° C.

For each sample a data file was generated which shows the total ion chromatogram for each sample. Integration of each peak was carried out through the ITD quantitation program, and a quantitation file was then generated for each sample. The data file for each sample was identified by the sample number .DAT. For example, Colombia marijuana sample #1 data file was designated as COMO1.DAT, the data file for Colombia marijuana sample #2 was designated COMO2.DAT, etc.. The quantitation file for each sample was designated as COMO1.QNT, COMO2.QNT, etc.

A normalization routine was used to transfer the quantitation report into a .TXT report which shows peak numbers and relative peak areas compared to the internal standard.

The .TXT files for the different samples could be directly compared since the intensity (peak area) of each peak in all samples are normalized relative to the internal standard.

EXAMPLE II

Chemical Profile of Cannabis Samples from Mexico

The same procedure described under Example I was used to generate chemical profiles for several Mexican marijuana samples. .DAT files, .QNT files, and .TXT files were generated for each sample.

EXAMPLE III

Chemical Profile of Cannabis Samples from Jamaica

The same procedure described under Example I was used to generate chemical profiles for several Jamaican marijuana samples. .DAT files, .QNT files, and .TXT files were generated for each sample.

EXAMPLE IV

Chemical Profile of Cannabis Samples from Thailand

The same procedure described under Example I was used to generate chemical profiles for several Thai marijuana samples. .DAT files, .QNT files) and .TXT files were generated for each sample.

EXAMPLE V

Chemical Profiles of Cannabis Samples from Different Locations in the United States The method outlined in Example I was used to generate the chemical profiles of marijuana samples confiscated in the States of Hawaii, California, Missouri, Kentucky, and Tennessee. .DAT files, .QNT files, and .TXT files were generated on each sample.

EXAMPLE VI

Composing Profiles for Cannabis Samples from Different Locations

A computer program was written which allowed the composition of a profile for a given geographical location by averaging the profiles of the individual samples from that location. The program allowed for the exclusion of samples which, for one reason or the other, did not fit into that profile. The program is based on the cosine similarity function and requires that sample-to-sample similarities within each profile be within the range of two standard deviations below the profile mean.

EXAMPLE VII

Comparision of Samples to Profiles

Once location profiles have been composed for the different locations (countries, etc.) the profile of an unknown sample may be compared to the location profiles and weighted best fit is obtained. A fit value of 1.0 represents a perfect fit while a 0.0 values represents no fit. The program would provide a fit value for the sample under investigation to each of the profiles used for the comparison.

We claim:

1. A method for determining country or location or contraband marijuana comprising the development of location profiles for Cannabis plant material samples from different countries or various geographical locations using capillary gas chromatographic analysis of extracts of the multiple plant material samples followed by detection and quantitation of the chromatographic peaks relative to an internal standard, composition of a "mean" profile and the use of the generated location profiles to compare with the profile of an unknown sample for source identification.

2. The method of claim 1 wherein said plant material is extracted with an organic solvent with an internal standard.

3. The method of claim 2 wherein said solvent is a mixture of methanol and chloroform in a ratio of 9:1 containing 0.2 mg/ml phenanthrene as internal standard.

4. The method of claim 1 wherein the chromatographic column is 30 M$\times$0.25 mm coated with a cross linked and bonded 100% dimethyl polysiloxane (0.25 mm) and the oven temperature thereof is programmed from 70° C.–250° C. at 5° C./min.

5. The method of claim 1 wherein the chromatographic peaks are detected using a mass spectrometer.

6. The method of claim 1 wherein the chromatographic peaks are detected using a flame ionization detector.

7. The method of claim 1 wherein the composite or "mean" location profile is computer generated taking into consideration all chromatographic peaks.

8. The method of claim 1 wherein the composite or "mean" location profile is computer generated taking into consideration only those peaks which have a significant contribution to the overall differences between location profiles.

9. The method of claim 1 wherein discriminant analysis is carried out using commercially available software programs which include statistical and pattern recognition algorithms.

10. The method of claim 1 wherein discriminant analysis for identification of the geographical origin of a given sample is carried out by visual inspection of the chromatograms for the presence or absence of specific peaks characteristic for a given geographical location.

* * * * *